US010767203B2

(12) United States Patent
Luo (10) Patent No.: US 10,767,203 B2
(45) Date of Patent: Sep. 8, 2020

(54) ARYLALKYLAMINE N-ACETYLTRANSFERASE AND USES THEREOF

(71) Applicant: DANMARKS TEKNISKE UNIVERSITET, Kgs. Lyngby (DK)

(72) Inventor: Hao Luo, Søborg (DK)

(73) Assignee: Danmarks Tekniske Universitet, Kgs. Lyngby (DK)

( * ) Notice: Subject to any disclaimer, the term of this patent is extended or adjusted under 35 U.S.C. 154(b) by 0 days.

(21) Appl. No.: 16/469,039

(22) PCT Filed: Dec. 13, 2017

(86) PCT No.: PCT/EP2017/082522
§ 371 (c)(1),
(2) Date: Jun. 12, 2019

(87) PCT Pub. No.: WO2018/108966
PCT Pub. Date: Jun. 21, 2018

(65) Prior Publication Data
US 2019/0352684 A1  Nov. 21, 2019

(30) Foreign Application Priority Data

Dec. 13, 2016 (EP) .................................. 16203711
Apr. 21, 2017 (EP) .................................. 17167508
Aug. 24, 2017 (WO) ................. PCT/EP2017/071381

(51) Int. Cl.
*C12P 17/10* (2006.01)
*C12N 9/10* (2006.01)
*C12N 15/70* (2006.01)

(52) U.S. Cl.
CPC ............ *C12P 17/10* (2013.01); *C12N 9/1029* (2013.01); *C12N 15/70* (2013.01); *C12Y 203/01087* (2013.01)

(58) Field of Classification Search
None
See application file for complete search history.

(56) References Cited

U.S. PATENT DOCUMENTS

2014/0134689 A1  5/2014  Lee et al.

FOREIGN PATENT DOCUMENTS

| EP | 0456507 | 5/1991 |
|---|---|---|
| WO | WO2013127915 | 9/2013 |
| WO | WO2015032911 | 3/2015 |
| WO | WO2017167866 | 10/2017 |
| WO | WO2017202897 | 11/2017 |

OTHER PUBLICATIONS

Ganguly, S. et al, Characterization of the *Saccharomyces cerevisiae* homolog of the melatonin rhythm enzyme arylalkyamine N-Acetyltransferase (EC 2.3.1.87), The Journal of Biological Chemistry, vol. 276, Issue Dec. 14, pp. 47239-47247, (2001).
Klein, D., "Arylalkylamine N-Acetyltransferase: the Timezyme", Journal of Biological Chemistry, vol. 282:7, pp. 4233-4238, (Feb. 16, 2007).
Kang, K. et al, "Molecular cloning of rice seratonin N-Acetyltransferase, the penultimate gene in plant melatonin biosynthesis", Journal of Pineal Research, vol. 55, pp. 7-13, (2013).
Li, M. et al, "A strategy of gene overexpression based on tandem repetitive promoters in *Escherichia coli*", Microbial Cell Facftories, vol. 11:19, pp. 1-10, (2012).
Liu, J. et al, "Unusual Acetylation-dependent reaction cascade in the biosynthesis of the Pyrroloindole drug Physostigmine**", Wiley Online Library, Angewandte Chem. Int. Ed., vol. 53, pp. 1-4, (2014).
McKenzie, G. et al, "Fast, easy and efficient: site-specific insertion of transgenes into Enterobacterial chromosomes using Tn7 without need for selection of the insertion event", BMC Microbiology, vol. 6:39, pp. 1-7, (Apr. 2006).
Okazaki, M. et al, "Cloning and characterization of a Chlamydomonas reinhardtii cDNA arylalkylamine N-acetyltransferase and its use in the genetic engineering of melatonin content in the Micro-Tom tomato", Journal of Pineal Research, vol. 46, pp. 373-382, (2009).
Thomas, K. et al, "Arylalkylamine (Serotonin) N-Acetyltransferase assay using high-performance liquid chromatography with fluorescence or eletrochemical detection of N-Acetyltryptamine", Analytical Biochemistry, vol. 184, pp. 228-234, (1990).
Anonymous, "Uniprot:X0ND19", retrieved from Internet: http://ibis.internal.epo.org/exam/dbfetch.jsp?id=UNIPROT: X0ND19, (retrieved Feb. 28, 2017).

*Primary Examiner* — Suzanne M Noakes
(74) *Attorney, Agent, or Firm* — McHale & Slavin, P.A.

(57) ABSTRACT

Described herein are variants of arylalkylamine N-acetyltransferase (AANAT) as well as vectors and recombinant microbial host cells expressing AANATs and variant AANATs and their use in producing N-acetylserotonin, melatonin and related compounds. Preferred AANAT variants provide for an increased yield of N-acetylserotonin.

20 Claims, 4 Drawing Sheets

Specification includes a Sequence Listing.

SEQUENCE LISTING

<160> NUMBER OF SEQ ID NOS: 6

<210> SEQ ID NO 1
<211> LENGTH: 182
<212> TYPE: PRT
<213> ORGANISM: Streptomyces griseofuscus

<400> SEQUENCE: 1

Met Asn Thr Phe Arg Thr Ala Thr Ala Arg Asp Ile Pro Asp Val Ala
1               5                   10                  15

Ala Thr Leu Thr Glu Ala Phe Ala Thr Asp Pro Pro Thr Gln Trp Val
            20                  25                  30

Phe Pro Asp Gly Thr Ala Ala Val Ser Arg Phe Phe Thr His Val Ala
            35                  40                  45

Asp Arg Val His Thr Ala Gly Gly Ile Val Glu Leu Leu Pro Asp Arg
 50                  55                  60

Ala Ala Met Ile Ala Leu Pro Pro His Val Arg Leu Pro Gly Glu Ala
 65                  70                  75                  80

Ala Asp Gly Arg Gln Ala Glu Ile Gln Arg Arg Leu Ala Asp Arg His
                 85                  90                  95

Pro Leu Thr Pro His Tyr Tyr Leu Leu Phe Tyr Gly Val Arg Thr Ala
            100                 105                 110

His Gln Gly Ser Gly Leu Gly Gly Arg Met Leu Ala Arg Leu Thr Ser
            115                 120                 125

Arg Ala Asp Arg Asp Arg Val Gly Thr Tyr Thr Glu Ala Ser Thr Trp
130                 135                 140

Arg Gly Ala Arg Leu Met Leu Arg His Gly Phe His Ala Thr Arg Pro
145                 150                 155                 160

Leu Arg Leu Pro Asp Gly Pro Ser Met Phe Pro Leu Trp Arg Asp Pro
                165                 170                 175

Ile His Asp His Ser Asp
            180

<210> SEQ ID NO 2
<211> LENGTH: 207
<212> TYPE: PRT
<213> ORGANISM: Bos taurus

<400> SEQUENCE: 2

Met Ser Thr Pro Ser Ile His Cys Leu Lys Pro Ser Pro Leu His Leu
1               5                   10                  15

Pro Ser Gly Ile Pro Gly Ser Pro Gly Arg Gln Arg Arg His Thr Leu
            20                  25                  30

Pro Ala Asn Glu Phe Arg Cys Leu Thr Pro Glu Asp Ala Ala Gly Val
            35                  40                  45

Phe Glu Ile Glu Arg Glu Ala Phe Ile Ser Val Ser Gly Asn Cys Pro
 50                  55                  60

Leu Asn Leu Asp Glu Val Arg His Phe Leu Thr Leu Cys Pro Glu Leu
65                  70                  75                  80

Ser Leu Gly Trp Phe Val Glu Gly Arg Leu Val Ala Phe Ile Ile Gly
                85                  90                  95

Ser Leu Trp Asp Glu Gly Arg Leu Thr Gln Glu Ser Leu Thr Leu His
            100                 105                 110

Arg Pro Gly Gly Arg Thr Ala His Leu His Ala Leu Ala Val His His
            115                 120                 125

Ser Phe Arg Gln Gln Gly Lys Gly Ser Val Leu Leu Trp Arg Tyr Leu
130                 135                 140

Gln His Ala Gly Gly Gln Pro Ala Val Arg Arg Ala Val Leu Met Cys
145                 150                 155                 160

Glu Asp Ala Leu Val Pro Phe Tyr Gln Arg Phe Gly Phe His Pro Ala
                165                 170                 175

Gly Pro Cys Ala Val Val Gly Ser Leu Thr Phe Thr Glu Met His
            180                 185                 190

Cys Ser Leu Arg Gly His Ala Ala Leu Arg Arg Asn Ser Asp Arg
            195                 200                 205

<210> SEQ ID NO 3
<211> LENGTH: 205
<212> TYPE: PRT
<213> ORGANISM: Gallus gallus

<400> SEQUENCE: 3

```
Met Pro Val Leu Gly Ala Val Pro Phe Leu Lys Pro Thr Pro Leu Gln
1               5                   10                  15

Gly Pro Arg Asn Ser Pro Gly Arg Gln Arg Arg His Thr Leu Pro Ala
            20                  25                  30

Ser Glu Phe Arg Cys Leu Ser Pro Glu Asp Ala Val Ser Val Phe Glu
        35                  40                  45

Ile Glu Arg Glu Ala Phe Ile Ser Val Ser Gly Asp Cys Pro Leu His
    50                  55                  60

Leu Asp Glu Ile Arg His Phe Leu Thr Leu Cys Pro Glu Leu Ser Leu
65                  70                  75                  80

Gly Trp Phe Glu Glu Gly Arg Leu Val Ala Phe Ile Ile Gly Ser Leu
                85                  90                  95

Trp Asp Gln Asp Arg Leu Ser Gln Ala Ala Leu Thr Leu His Asn Pro
            100                 105                 110

Arg Gly Thr Ala Val His Ile His Val Leu Ala Val His Arg Thr Phe
        115                 120                 125

Arg Gln Gln Gly Lys Gly Ser Ile Leu Met Trp Arg Tyr Leu Gln Tyr
    130                 135                 140

Leu Arg Cys Leu Pro Cys Ala Arg Arg Ala Val Leu Met Cys Glu Asp
145                 150                 155                 160

Phe Leu Val Pro Phe Tyr Glu Lys Cys Gly Phe Val Ala Val Gly Pro
                165                 170                 175

Cys Gln Val Thr Val Gly Thr Leu Ala Phe Thr Glu Met Gln His Glu
            180                 185                 190

Val Arg Gly His Ala Phe Met Arg Arg Asn Ser Gly Cys
        195                 200                 205
```

<210> SEQ ID NO 4
<211> LENGTH: 207
<212> TYPE: PRT
<213> ORGANISM: Oryctolagus cuniculus

<400> SEQUENCE: 4

```
Met Ser Thr Leu Ser Thr Gln Pro Leu Lys Pro Lys Ala Leu His Pro
1               5                   10                  15

Pro Pro Gly Ser Pro Glu Ser Pro Gly His Gln Arg Arg His Thr Leu
            20                  25                  30

Pro Ala Ser Glu Phe Arg Cys Leu Thr Pro Glu Asp Ala Ala Gly Val
        35                  40                  45

Phe Glu Ile Glu Arg Glu Ala Phe Met Ser Val Ser Gly Ser Cys Pro
    50                  55                  60

Leu Tyr Leu Asp Glu Ile Arg His Phe Leu Thr Leu Cys Pro Glu Leu
65                  70                  75                  80

Ser Leu Gly Trp Phe Gln Glu Gly Arg Leu Val Ala Phe Ile Ile Gly
                85                  90                  95

Ser Leu Trp Asp Lys Glu Arg Leu Thr Gln Glu Ser Leu Thr Leu His
            100                 105                 110

Arg Pro Gly Gly Arg Val Ala His Leu His Val Leu Ala Val His Arg
        115                 120                 125

Ala Cys Arg Gln Gln Gly Lys Gly Ser Val Leu Leu Trp Arg Tyr Leu
```

```
                130             135             140
Gln His Leu Gly Gly Gln Arg Ala Val Arg Arg Ala Val Leu Met Cys
145                 150                 155                 160

Glu Asp Ala Leu Val Pro Phe Tyr Glu Arg Leu Gly Phe Arg Ala Val
                165                 170                 175

Gly Pro Cys Ala Val Thr Val Gly Ser Leu Ala Phe Thr Glu Leu Gln
                180                 185                 190

Cys Ser Val Arg Gly His Ala Cys Leu Arg Arg Lys Ser Gly Cys
                195                 200                 205

<210> SEQ ID NO 5
<211> LENGTH: 205
<212> TYPE: PRT
<213> ORGANISM: Mus musculus

<400> SEQUENCE: 5

Met Leu Asn Ile Asn Ser Leu Lys Pro Glu Ala Leu His Leu Pro Leu
1               5                   10                  15

Gly Thr Ser Glu Phe Leu Gly Cys Gln Arg Arg His Thr Leu Pro Ala
                20                  25                  30

Ser Glu Phe Arg Cys Leu Thr Pro Glu Asp Ala Thr Ser Ala Phe Glu
            35                  40                  45

Ile Glu Arg Glu Ala Phe Ile Ser Val Ser Gly Thr Cys Pro Leu Tyr
50                  55                  60

Leu Asp Glu Ile Arg His Phe Leu Thr Leu Cys Pro Glu Leu Ser Leu
65                  70                  75                  80

Gly Trp Phe Glu Glu Gly Cys Leu Val Ala Phe Ile Ile Gly Ser Leu
                85                  90                  95

Trp Asp Lys Glu Arg Leu Thr Gln Glu Ser Leu Thr Leu His Arg Pro
                100                 105                 110

Gly Gly Arg Thr Ala His Leu His Val Leu Ala Val His Arg Thr Phe
            115                 120                 125

Arg Gln Gln Gly Lys Gly Ser Val Leu Leu Trp Arg Tyr Leu His His
130                 135                 140

Leu Gly Ser Gln Pro Ala Val Arg Arg Ala Val Leu Met Cys Glu Asp
145                 150                 155                 160

Ala Leu Val Pro Phe Tyr Glu Lys Phe Gly Phe Gln Ala Val Gly Pro
                165                 170                 175

Cys Ala Ile Thr Val Gly Ser Leu Thr Phe Thr Glu Leu Gln Cys Ser
                180                 185                 190

Leu Arg Cys His Ala Phe Leu Arg Arg Asn Ser Gly Cys
                195                 200                 205

<210> SEQ ID NO 6
<211> LENGTH: 207
<212> TYPE: PRT
<213> ORGANISM: Homo sapiens

<400> SEQUENCE: 6

Met Ser Thr Gln Ser Thr His Pro Leu Lys Pro Glu Ala Pro Arg Leu
1               5                   10                  15

Pro Pro Gly Ile Pro Glu Ser Pro Ser Cys Gln Arg Arg His Thr Leu
                20                  25                  30

Pro Ala Ser Glu Phe Arg Cys Leu Thr Pro Glu Asp Ala Val Ser Ala
                35                  40                  45

Phe Glu Ile Glu Arg Glu Ala Phe Ile Ser Val Leu Gly Val Cys Pro
```

-continued

```
              50                  55                  60
Leu Tyr Leu Asp Glu Ile Arg His Phe Leu Thr Leu Cys Pro Glu Leu
 65                  70                  75                  80

Ser Leu Gly Trp Phe Glu Glu Gly Cys Leu Val Ala Phe Ile Ile Gly
                 85                  90                  95

Ser Leu Trp Asp Lys Glu Arg Leu Met Gln Glu Ser Leu Thr Leu His
                100                 105                 110

Arg Ser Gly Gly His Ile Ala His Leu His Val Leu Ala Val His Arg
                115                 120                 125

Ala Phe Arg Gln Gln Gly Arg Gly Pro Ile Leu Leu Trp Arg Tyr Leu
                130                 135                 140

His His Leu Gly Ser Gln Pro Ala Val Arg Arg Ala Ala Leu Met Cys
145                 150                 155                 160

Glu Asp Ala Leu Val Pro Phe Tyr Glu Arg Phe Ser Phe His Ala Val
                165                 170                 175

Gly Pro Cys Ala Ile Thr Val Gly Ser Leu Thr Phe Met Glu Leu His
                180                 185                 190

Cys Ser Leu Arg Gly His Pro Phe Leu Arg Arg Asn Ser Gly Cys
                195                 200                 205
```

ARYLALKYLAMINE N-ACETYLTRANSFERASE AND USES THEREOF

FIELD OF THE INVENTION

The present invention relates to *Streptomyces griseofuscus* arylalkylamine N-acetyltransferase (AANAT) and variants thereof, as well as their use in producing N-acetylserotonin and/or melatonin.

BACKGROUND OF THE INVENTION

Melatonin (N-acetyl-5-methoxy tryptamine), is a substance found in all animals as well as in plants, fungi, and bacteria. Melatonin is a powerful antioxidant and maintains the body's circadian rhythm. At least in vertebrates, melatonin is biosynthesized from the native metabolite L-tryptophan via the intermediates 5-hydroxy-L-tryptophan (5HTP), serotonin (a.k.a. 5-hydroxytryptamine) and N-acetylserotonin, with the conversion of serotonin to N-acetylserotonin being catalyzed by AANAT (EC 2.1.3.87).

Klein et al. (2007) provides an overview of the biological chemistry of AANAT, describing, e.g., that AANAT family members have been found in Gram-positive bacteria, fungi, algae, cephalochordates, and vertebrates. Further, Liu et al. (2014) identified a biosynthetic gene cluster in *Streptomyces griseofuscus* encoding eight proteins catalyzing the biosynthesis of physostigmine from 5-hydroxytryptophan. Based on in vitro assays, one of the proteins, PsmF (SEQ ID NO:1), was reported to function as a (serotonin) N-acetyltransferase.

Over-the-counter dietary supplements based on chemically synthesized melatonin have been available for many years in the U.S. Melatonin can also be produced in microbial cells engineered to express an appropriate biosynthetic pathway (see, e.g., WO 2013/127915 A1, WO 2015/032911 A1 and US 2014/134689 AA). For cost-effective production of bulk chemicals in microbial hosts, however, high product titers are essential. Accordingly, there is a need for optimizing AANAT activity in microbial host cells, for production of N-acetylserotonin, melatonin and related chemicals.

The present invention addresses these and other needs in the art.

SUMMARY OF THE INVENTION

The present inventor has found that AANAT from *S. griseofuscus* (esgAANAT; SEQ ID NO:1) is more effective in vivo than a range of vertebrate AANATs. Moreover, mutations in sgAANAT which increased the in vivo turnover of were identified.

Accordingly, in one aspect, the invention relates to a variant sgAANAT comprising a mutation in the residue corresponding to D63.

In other aspects, nucleic acid sequences and vectors encoding such variant AANATs are provided.

In still other aspects, native or variant sgAANAT is expressed in recombinant host cells, e.g., from a chromosomally integrated gene. The recombinant host cell may, for example, be derived from an *E. coli* cell and comprise a heterologous biosynthetic pathway for producing serotonin, N-acetylserotonin and/or melatonin.

Other aspects herein relate to the use of such recombinant host cells for producing N-acetylserotonin and/or melatonin.

These and other aspects and embodiments are described in more detail below.

DETAILED DISCLOSURE OF THE INVENTION

As shown in Example 1, surprisingly, sgAANAT was significantly more effective in vivo than 5 AANATs from vertebrate sources in promoting N-acetylation of serotonin, and its activity would be further improved by engineering specific residues, particularly residue D63.

In one aspect, the invention relates to a catalytically active variant of sgAANAT, the variant comprising a mutation in residue D63 and providing for an increased yield in vivo of N-acetylserotonin from serotonin relative to native enzyme. The D63 mutation may, for example, be an amino acid substitution selected from D63G, D63A, D63V, D63L and D63I. In a specific embodiment, the mutation is D63G. In some embodiments, the catalytically active variant has at least 85% sequence identity to SEQ ID NO:1.

In other aspects, the invention relates to a nucleic acid sequence encoding such a variant sgAANAT; a vector comprising such a nucleic acid sequence and, optionally, one or more elements that promote integration of the nucleic acid sequence into the host cell genome; and to a recombinant host cell comprising such a variant AANAT, nucleic acid sequence and/or vector. In a specific embodiment, the nucleic acid sequence is chromosomally integrated. Examples of host cells include those derived from a mammalian cell, a bacterial cell, a yeast cell, a filamentous fungal cell or an algal cell. Preferably, the host cell is derived from an *Escherichia* cell or an *S. cerevisiae* cell. In another aspect, the invention relates to a process for preparing the recombinant host cell of any aspect, comprising transforming a host cell with the vector.

In another aspect, the invention relates to a recombinant host cell which is derived from an *E. coli* or *S. cerevisiae* cell, comprising a chromosomally integrated gene encoding sgAANAT or a catalytically active fragment or variant thereof. The catalytically active variant may, for example, comprise a D63G amino acid substitution.

The recombinant host cell of any aspect may further comprise a native or heterologous biosynthetic pathway for producing serotonin and, optionally, an acetylserotonin O-methyltransferase (ASMT).

In another aspect, the invention relates to a method of producing N-acetylserotonin, comprising culturing a recombinant host cell of any aspect in a medium comprising a carbon source, and, optionally, isolating N-acetylserotonin.

In another aspect, the invention relates to a method of producing melatonin, comprising culturing the recombinant host cell of any aspect in a medium comprising a carbon source, and, optionally, isolating melatonin, wherein the recombinant host cell comprises an ASMT.

Definitions

Unless otherwise specified or contradicted by context, "*Streptomyces griseofuscus* AANAT", "*S. griseofuscus* AANAT" or "sgAANAT" herein refers to the sequence provided by Uniprot reference W8QGX9 and Genbank AHL44344.1 (SEQ ID NO:1).

AANAT is the abbreviation of arylalkylamine N-acetyltransferase, also known as serotonin N-acetyltransferase, and generally classified under Enzyme Commission (EC) number EC 2.3.1.87 or 2.3.1.5.

As used herein, "exogenous" means that the referenced item, such as a molecule, activity or pathway, is added to or introduced into the host cell or microorganism. An exogenous nucleic acid sequence can, for example, be introduced either as chromosomal genetic material by integration into a host chromosome or as non-chromosomal genetic material such as a plasmid. Such an exogenous nucleic acid sequence can encode an enzyme or enzyme activity which is either heterologous to the host cell or organism in question or which is an endogenous enzyme or enzyme activity in the host cell or organism. Likewise, an exogenous molecule such as a substrate or cofactor can be added to or introduced into the host cell or microorganism, e.g., via adding the molecule to the media in or on which the host cell or microorganism resides.

In the present context the term "heterologous" means that the referenced item, such as a molecule, activity or pathway, does not normally appear in the host cell or microorganism species in question. Typically, a heterologous pathway comprises at least one enzyme or other component which is heterologous to the host cell.

As used herein, the terms "native" or "endogenous" mean that the referenced item is normally present in or native to the host cell or microbial species in question.

As used herein, "upregulating" an endogenous gene means increasing the transcription and/or translation of a gene present in the native host cell genome relative to a control, such as e.g. the unmodified host cell. Methods of upregulating genes are known in the art and include, e.g., introducing a non-native promoter increasing transcription, modifying the native promoter, deleting genes encoding repressor protein, introducing multiple copies of the gene of interest, etc. "Downregulating" an endogenous gene as used herein means to reduce, optionally eliminate, the transcription or translation of an endogenous gene relative to a control, such as, e.g., the unmodified host cell. Methods of down-regulating, disrupting and deleting genes are known to those of skill in the art, and include, e.g., site-directed mutagenesis, genomic modifications based on homologous recombination, RNA degradation based on CAS9, etc.

In the present context, "overexpressing" refers to introducing an exogenous nucleic acid sequence encoding an enzyme which is either heterologous or native to the microbial host cell, or is a catalytically active fragment or variant thereof, and expressing the exogenous nucleic acid sequence to increase the enzyme activity in the microbial cell as compared to the microbial host cell without the introduced exogenous nucleic acid sequence, e.g., a native microbial host cell. This can be useful if, e.g., a microbial host cell does not normally contain the enzymatic activity referred to, where the native enzymatic activity is insufficient, or the native enzyme is subjected to unwanted regulation. In such cases, an exogenous nucleic acid sequence encoding an enzyme which is heterologous to the microbial host cell and which has the desired activity and regulation patterns can be introduced. Overexpression of a nucleic acid sequence can be achieved by placing the nucleic acid sequence under the control of a strong promoter. Non-limiting examples of strong promoters suitable for, e.g., *E. coli* cells are Ptrc, Plac, PlacUV5, PT7, and PTrp. Non-limiting examples of strong promoters suitable for, e.g., yeast cells are TEF1, PGK1, HXT7 and TDH3.

As used herein, a gene that is a "homolog" or "homologous" to another gene is generally an ortholog (i.e., a descended from the same ancestral sequence but separated when a species diverges into two separate species) or a paralog (i.e., separated by gene duplication within a genome). Typically, homologous genes encode proteins with a moderate to high sequence identity (e.g., at least about 30%, such as at least about 50%, such as at least about 60%, such as at least about 70%, such as at least about 80%, such as at least about 90%, such as at least about 95%, such as at least about 99%, over at least the catalytically active portion, optionally over the full length) and/or can at least partially substitute for the other protein in terms of function, when transferred from one species into another. Homologs of a particular gene can be identified using publicly available and specialized biological databases, e.g., by the eggNOG, InParanoid, OrthoDB, OrthoMCL, OMA, Roundup, TreeFam, LOFT, Ortholuge, EnsemblCompara GeneTrees and HomoloGene.

A "variant" of a parent or reference enzyme comprises one or more mutations, such as amino acid substitutions, insertions and deletions, as compared to the parent or reference enzyme. Typically, the variant has a high sequence identity to the amino acid sequence of the parent or reference enzyme (e.g., at least about 70%, such as at least about 80%, such as at least 84%, such as at least 85%, such as at least 87%, such as at least about 90%, such as at least about 93%, such as at least about 95%, such as at least about 96%, such as at least about 97%, such as at least about 98%, such as at least about 99%, over at least the catalytically active portion, optionally over the full length).

Unless otherwise stated, the term "sequence identity" for amino acid sequences as used herein refers to the sequence identity calculated as $(n_{ref}-n_{dif})\cdot 100/n_{ref}$ wherein $n_{dif}$ is the total number of non-identical residues in the two sequences when aligned and wherein $n_{ref}$ is the number of residues in one of the sequences. Hence, the amino acid sequence GSTDYTQNWA will have a sequence identity of 80% with the sequence GSTGYTQAWA ($n_{dif}=2$ and $n_{ref}=10$). The sequence identity can be determined by conventional methods, e.g., Smith and Waterman, (1981), Adv. Appl. Math. 2:482, by the 'search for similarity' method of Pearson & Lipman, (1988), Proc. Natl. Acad. Sci. USA 85:2444, using the CLUSTAL W algorithm of Thompson et al., (1994), Nucleic Acids Res 22:467380, by computerized implementations of these algorithms (GAP, BESTFIT, FASTA, and TFASTA in the Wisconsin Genetics Software Package, Genetics Computer Group). The BLAST algorithm (Altschul et al., (1990), Mol. Biol. 215:403-10) for which software may be obtained through the National Center for Biotechnology Information www.ncbi.nlm.nih.gov/) may also be used. When using any of the aforementioned algorithms, the default parameters for "Window" length, gap penalty, etc., are used.

A residue in one amino acid sequence which "corresponds to" a specific reference residue in a reference amino acid sequence is the residue which aligns with the reference residue.

A "fragment" of a protein comprises at least the part of the protein which is responsible for its function of interest, e.g., in the case of an enzyme, its catalytic part. Typically, a "fragment" comprises a segment corresponding to at least about 30%, such as at least about 50%, such as at least about 60%, such as at least about 70%, such as at least about 80%, such as at least about 90%, such as at least about 95%, of the full length protein.

A "functionally active variant" or "functionally active fragment" comprises mutations and/or deletions, respectively, which do not substantially affect the function of the variant or fragment as compared to the parent or reference protein, and can substitute at least partially for the parent or reference protein in terms of the function of interest. Typically, in the case of an enzyme, a functionally active variant or fragment is a "catalytically active" variant or fragment, having a catalytic activity, as determined by a suitable activity assay, which is 50-150%, such as 80-120%, such as 90%-110%, such as 95%-105%, of that of the parent or reference enzyme (which may in itself be a variant of a native enzyme).

As used herein, "vector" refers to any genetic element capable of serving as a vehicle of genetic transfer, expression, or replication for an exogenous nucleic acid sequence in a host cell. For example, a vector may be an artificial chromosome or a plasmid, and may be capable of stable integration into a host cell genome, or it may exist as an independent genetic element (e.g., episome, plasmid). A vector may exist as a single nucleic acid sequence or as two or more separate nucleic acid sequences. Vectors may be single copy vectors or multicopy vectors when present in a host cell. Preferred vectors for use in the present invention are expression vector molecules in which one or more functional genes can be inserted into the vector molecule, in proper orientation and proximity to expression control elements resident in the expression vector molecule so as to direct expression of one or more proteins when the vector molecule resides in an appropriate host cell.

Standard recombinant DNA and molecular cloning techniques useful for construction of appropriate expression vectors and other recombinant or genetic modification techniques for practising the invention, are well known in the art and are described by, e.g., Green and Sambrook, Molecular Cloning, A Laboratory Manual, Cold Spring Harbor Laboratory Press (Cold Spring Harbor, N.Y.) (2012); by Silhavy, T. J., Bennan, M. L. and Enquist, L. W. Experiments with Gene Fusions; Cold Spring Harbor Laboratory: Cold Spring Harbor, N.Y., 1984; by Ausubel et al., Short Protocols in Molecular Biology, Current Protocols, John Wiley and Sons (New Jersey) (2002), and references cited herein. Appropriate microbial cells and vectors are available commercially through, for example, the American Type Culture Collection (ATCC), Rockville, Md.

The term "host cell" refers to any cell into which an exogenous nucleic acid sequence can be introduced and expressed, typically via an expression vector. The host cell may, for example, be a wild-type cell isolated from its natural environment, a mutant cell identified by screening, a cell of a commercially available strain, or a genetically engineered cell or mutant cell, comprising one or more other exogenous and/or heterologous nucleic acid sequences than those of the invention.

A "recombinant" cell or host cell as used herein refers to a host cell into which one or more exogenous nucleic acid sequences of the invention have been introduced, typically via transformation of a host cell with a vector.

The term "substrate" or "precursor", as used herein in relation to a specific enzyme, refers to a molecule upon which the enzyme acts to form a product. When used in relation to an exogenous biometabolic pathway, the term "substrate" or "precursor" refers to the molecule(s) upon which the first enzyme of the referenced pathway acts. When referring to an enzyme-catalyzed reaction in a microbial cell, an "endogenous" substrate or precursor is a molecule which is native to or biosynthesized by the microbial cell, whereas an "exogenous" substrate or precursor is a molecule which is added to the microbial cell, via a medium or the like.

Enzymes referred to herein can be classified on the basis of the handbook Enzyme Nomenclature from NC-IUBMB, 1992), see also the ENZYME site at the internet: www.expasy.ch/enzyme/. This is a repository of information relative to the nomenclature of enzymes, and is primarily based on the recommendations of the Nomenclature Committee of the International Union of Biochemistry and Molecular Biology (IUB-MB). It describes each type of characterized enzyme for which an EC (Enzyme Commission) number has been provided (Bairoch A., The ENZYME database, 2000, Nucleic Acids Res 28:304-305). The IUBMB Enzyme nomenclature is based on the substrate specificity and occasionally on their molecular mechanism.

Specific Embodiments of the Invention

Figure 1:
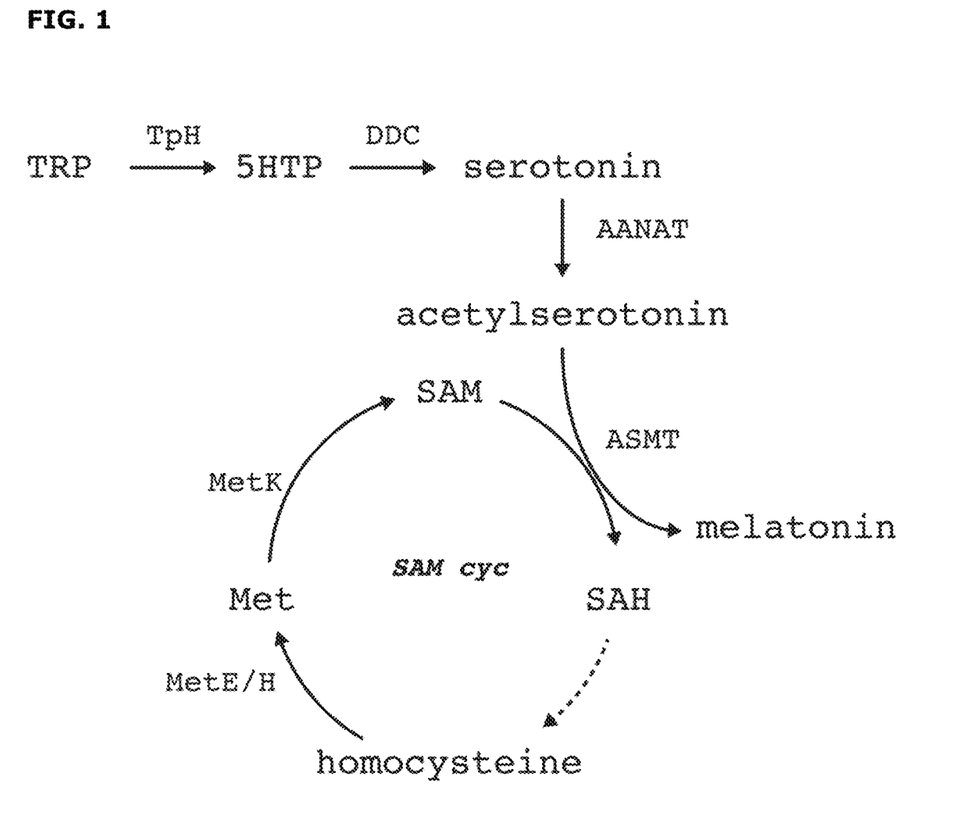
FIG. 1: Metabolic pathways for the production of serotonin, N-acetylserotonin and/or melatonin. TRP= tryptophan; Met=methionine; SAM=S-adenosyl methionine; SAH=S-S-adenosyl homocysteine.

Preferred AANAT variants and AANAT-expressing host cells are described below, as well as other enzymes in preferred biosynthetic pathways for production of melatonin in recombinant microbial cells. A preferred example of such a pathway is shown in FIG. 1, comprising an L-tryptophan hydroxylase (TPH), a 5HTP decarboxylase, an AANAT as provided herein, and, optionally, an acetylserotonin O-methyltransferase (ASMT).

Arylalkylamine N-acetyltransferase (AANAT)

AANATs are typically classified under EC number EC 2.3.1.87 or 2.3.1.5. AANATs suitable for melatonin-production via to the metabolic pathway of FIG. 1 catalyze the acetylation of serotonin in the presence of Acetyl coenzyme A (also referred to as acetyl-CoA or AcCoA—see FIG. 1). Particularly preferred for use in E. coli and other microbial host cells is sgAANAT (SEQ ID NO:1) and catalytically active variants, homologs and fragments thereof.

Catalytically active fragments and variants of sgAANAT can be identified by a person of skill in the art. For example, to increase heterologous expression in E. coli and/or the enzyme stability, the sgAANAT sequence can be truncated to remove portions not needed for its catalytic activity while preserving the catalytic core of the enzyme, e.g., by 1, 2, 3, 4, 5, 10, 20 or more amino acid residues from the C-terminal, N-terminal, or both. In addition, variants of sgAANAT comprising one or more amino acid substitutions, deletions or insertions can also be used. In separate and specific embodiments, the sgAANAT variant comprises up to 10 mutations, such as 1, 2, 3, 4, 5, 6, 7, 8, 9 or 10 mutations. In a preferred embodiment, the sgAANAT variant comprises a mutation in amino acid D63, such as an amino acid substitution. Preferably, the amino acid substitution is selected from D63G, D63A, D63V, D63L and D63I, most preferably D63G.

As described in Example 1, an amino acid substitution in D63 provided for an increased yield in vivo of N-acetylserotonin from serotonin relative to native the enzyme. Accordingly, sgAANAT variants comprising an amino acid substitution in D63, such as e.g. D63G, are particularly preferred. In addition to the amino acid substitution in D63, such sgAANAT variants may further comprise 1, 2, 3, 4, 5, 6, 7, 8 or 9 or more additional mutations, such as conservative amino acid substitutions, so long as the sgAANAT variant provides for substantially the same or a higher yield in vivo of N-acetylserotonin from serotonin relative to the native sgAANAT enzyme or relative to full-length sgAANAT comprising only a D63G mutation. In addition, a sgAANAT variant comprising an amino acid substitution in D63G and any additional mutations may be a fragment, so long as the fragment provides for substantially the same or a higher yield in vivo of N-acetylserotonin from serotonin relative to native sgAANAT or full-length sgAANAT with a D63G mutation. This can be tested according to one of the assays described in Example 1, e.g., integrating the coding gene of the sgAANAT fragment or variant into the genome of an *E. coli* host cell under the control of a Trc promoter, and comparing the yield of N-acetylserotonin from added serotonin with a control, e.g. native sgAANAT or sgAANAT with a D63G mutation. Alternatively, the variant or fragment sgAANAT and the control enzyme can be expressed from plasmids, as described in Examples 1 and 2. Other suitable assays for testing N-acetylserotonin production by an AANAT in a recombinant microbial host cell are known in the art and described in, e.g., Thomas et al., Analytical Biochemistry 1990; 184:228-34.

Typically, the sgAANAT variant has at least about 70%, such as at least about 80%, such as at least 84%, such as at least 85%, such as at least 87%, such as at least about 90%, such as at least about 93%, such as at least about 95%, such as at least about 96%, such as at least about 97%, such as at least about 98%, such as at least about 99% sequence identity at least the catalytically active portion of SEQ ID NO:1, optionally over the full length of SEQ ID NO:1. In a specific embodiment, the sgAANAT variant comprises or consists of SEQ ID NO:1 having a D63G mutation. In another specific embodiment, the sgAANAT variant is a catalytically active fragment of SEQ ID NO:1 having a D63G mutation.

Accordingly, such assays can be used to identify mutations and/or truncations providing for an increased or retained AANAT activity. For example, the assay can be used to identify sgAANAT fragments or variants providing for a retained or higher turnover rate or a retained higher total yield in the referenced reaction as compared to a control value, e.g., the turnover rate or total yield of the native sgAANAT in the same assay. Preferably, for an sgAANAT variant comprising an amino acid substitution in D63 and/or other mutations, the turnover rate or total yield is at least about 5% higher, at least about 10% higher, at least about 20% higher, at least about 25% higher, at least about 50% higher (i.e., at least about 1.5-fold), at least about 100% higher (i.e., at least about 2-fold), at least about 150% higher (i.e., at least about 2.5-fold), at least about 200% higher (i.e., at least about 3-fold), or at least about 300% higher (i.e., at least about 4-fold), or at least about 400% higher (i.e., at least about 5-fold) than the control, e.g., the turnover rate or total yield when using the native sgAANAT.

Nucleic acid sequences and vectors encoding sgAANAT or catalytically active fragments or variants thereof as described herein, as well as recombinant host cells expressing sgAANAT or catalytically active fragments or variants thereof from such nucleic acid sequences or vectors, are also contemplated. In one embodiment, the nucleic acid sequence encoding the sgAANAT is operably linked to a strong promoter such as the Trc promoter, providing for high expression levels of the AANAT in an *E. coli* host. Optionally, the vectors further comprise elements that promote integration of the nucleic acid sequences into the host cell genome. Accordingly, recombinant host cells wherein the nucleic acid sequences are chromosomally integrated are also contemplated.

L-Tryptophan Hydroxylase (TPH)

Sources of nucleic acid sequences encoding a TPH include any species where the encoded gene product is capable of catalyzing the referenced reaction, including humans, mammals such as, e.g., mouse, cow, horse, chicken and pig, as well as other animals such as, e.g., the parasite *Schistosoma mansoni*. In humans and, it is believed, in other mammals, there are two distinct TPH alleles, referred to herein as TPH1 and TPH2, respectively. As shown in FIG. 1, TPHs may require a cofactor; tetrahydrobiopterin (THB, alternatively abbreviated as BH4). It has been reported, however, that native tetrahydromonapterin (MH4) can replace or substitute for THB as a TPH cofactor (US 2014/0134689 AA).

Examples of nucleic acids encoding L-tryptophan hydroxylase for use in aspects and embodiments of the present invention include, but are not limited to, those encoding the TPHs listed in Table 1, as well as catalytically active variants, homologs and fragments thereof.

Catalytically active fragments and variants of TPH enzymes are known in the art. For example, to increase heterologous expression in *E. coli* and the enzyme stability, the TPH sequence can be truncated to remove portions not needed for its catalytic activity which preserving the catalytic core of the enzyme. Specific examples of catalytically active fragments of TPH include Met102 to Ser416 of *Oryctolagus cuniculus* TPH (Moran et al., J Biol Chem 1998; 273(20): 12259-66) and residues Asp45-Arg471 or Glu147-Thr460 (i.e., E147 to I460) of *Homo sapiens* TPH2, optionally adding an N-terminal methionine residue. Other useful TPH variants are described in WO 2017/167866, hereby incorporated by reference in its entirety. Other TPH sequences can be similarly truncated to create catalytically active fragments or variants comprising the catalytic core. *Homo sapiens* TPH2, or a catalytically active fragment and/or variant thereof is particularly preferred. Notably, *Schistosoma mansoni* TPH (see Table 1) has advantageous properties with respect to, e.g., solubility, thus enabling no or less truncation of the enzyme sequence. Accordingly, *Schistosoma mansoni* TPH, or a catalytically active fragment and/or variant thereof, can also be used.

Assays for measuring L-tryptophan hydroxylase activity in vitro are well-known in the art (see, e.g., Winge et al., Biochem J, 2008; 410:195-204 and Moran et al., 1998). In the recombinant host cell, the L-tryptophan hydroxylase is typically sufficiently expressed so that an increased level of 5HTP production from L-tryptophan can be detected as compared to the microbial host cell prior to transformation with the TPH, optionally in the presence of added cofactor and/or tryptophan substrate. Alternatively, the expression level of the specific TPH enzyme can be evaluated by proteomic analysis, according to methods known in the art. In a preferred embodiment, the nucleic acid sequence encoding the TPH is operably linked to a strong promoter such as the Trc promoter, providing for high expression levels of the TPH.

5HTP Decarboxylase

The last step in the serotonin biosynthesis via a 5HTP intermediate, the conversion of 5HTP to serotonin, is in animal cells catalyzed by a 5HTP decarboxylase, which is an aromatic L-amino acid decarboxylase (AADC) typically classified as EC 4.1.1.28. Suitable 5HTP decarboxylases include any tryptophan decarboxylase (TDC) capable of catalyzing the referenced reaction. TDC participates in the plant serotonin biosynthesis pathway, where tryptophan decarboxylase (TDC) catalyzes the conversion of tryptophan to tryptamine, which is then converted into serotonin in a reaction catalyzed by tryptamine 5-hydroxylase (T5H). TDC likewise belongs to the aromatic amino acid decarboxylases categorized in EC 4.1.1.28, and can be able to convert 5HTP to serotonin and carbon dioxide (see, e.g., Park et al., Biosci. Biotechnol. Biocem. 2008; 72(9):2456-2458.2008, and Gibson et al., J. Exp. Bot. 1972; 23(3):775-786), and thus function as a 5HTP decarboxylase. Exemplary nucleic acids encoding ADDC enzymes for use in aspects and embodiments of the present invention include, but are not limited to, those encoding the 5HTP decarboxylases listed in Table 1, as well as catalytically active variants, homologs and fragments thereof. In some embodiments, particularly where it is desired to also promote serotonin formation from a tryptamine substrate in the same recombinant cell, an enzyme capable of catalyzing both the conversion of tryptophan to tryptamine and the conversion of 5HTP to serotonin can be used. For example, rice TDC and tomato TDC can function also as a 5HTP decarboxylase, an activity which can be promoted by the presence of pyridoxal phosphate (e.g., at a concentration of about 0.1 mM) (Park et al., 2008). Preferred, non-limiting sources of 5HTP decarboxylase include Candidatus Koribacter versatilis Ellin345, Draconibacterium orientale and Verrucosispora maris (Table 1).

Suitable assays for testing serotonin production by a 5HTP decarboxylase in a recombinant microbial host cell are provided in, or can be adapted from, e.g., Park et al. (2008) and Park et al., Appl Microbiol Biotechnol 2011; 89(5):1387-1394. For example, these assays can be adapted to test serotonin production by a 5HTP decarboxylase (e.g., a TDC), either from 5HTP or, in case the microbial cell comprises an L-tryptophan hydroxylase, from L-tryptophan (or simply a carbon source). In the recombinant host cell, the 5HTP decarboxylase is typically sufficiently expressed so that an increased level of serotonin production can be detected as compared to the microbial host cell prior to transformation with the 5HTP decarboxylase. Alternatively, the expression level of the specific 5HTP decarboxylase can be evaluated by proteomic analysis, according to methods known in the art. In a preferred embodiment, the nucleic acid sequence encoding the 5HTP decarboxylase is operably linked to a strong promoter such as the Trc promoter, providing for high expression levels of the 5HTP decarboxylase.

Acetylserotonin O-Methyltransferase (ASMT):

In one aspect, the recombinant cell further comprises an exogenous nucleic acid encoding an acetylserotonin O-methyltransferase or ASMT, typically classified as EC 2.1.1.4. ASMT catalyzes the last reaction in the production of melatonin from L-tryptophan, the conversion of N-acetylserotonin and S-adenosyl-L-methionine (SAM) to Melatonin and S-adenosyl-L-homocysteine (SAH). SAH can then be recycled back to SAM via the S-adenosyl-L-methionine cycle in microbial cells where the S-adenosyl-L-methionine cycle is native (or exogenously added) and constitutively expressed, such as, e.g., in E. coli.

Sources of nucleic acid sequences encoding a native ASMT include any species where the encoded gene product is capable of catalyzing the referenced reaction, including humans and other mammalian and non-mammalian animals, plants, etc. Examples of nucleic acids encoding ASMT for use in aspects and embodiments of the present invention include, but are not limited to, those encoding the ASMTs listed in Table 1, as well as catalytically active variants, homologs and fragments thereof. ASMTs particularly suitable for E. coli and other microbial host cells include Homo sapiens, Ocimum basilicum, Bos Taurus, Takifugu rubripes, Macaca mulatta and Elephantulus edwardii ASMT. Particularly preferred is hsASMT. Useful ASMTs and variants of ASMT are described in WO 2017/202897, hereby incorporated by reference in its entirety.

Suitable assays for testing melatonin production by an ASMT in vitro or in a recombinant microbial host cell include the assay described in Kang et al. J. Pineal Res. 2011:50; 304-309. In the recombinant host cell, the ASMT is typically sufficiently expressed so that an increased level of melatonin production can be detected as compared to the microbial host cell prior to transformation with the ASMT. Alternatively, the expression level of the specific ASMT can be evaluated by proteomic analysis, according to methods known in the art. In a preferred embodiment, the nucleic acid sequence encoding the ASMT is operably linked to a strong promoter such as the Trc promoter, providing for high expression levels of the ASMT.

TABLE 1

Examples of enzymes and amino acid sequences

| Name (EC #) | Species | Genbank or UniProtKB accession No. (SEQ ID) |
|---|---|---|
| L-tryptophan hydroxylase (EC 1.14.16.4) (TPH) | Oryctolagus cuniculus TPH1 | P17290-1, v2 |
| | Homo sapiens TPH1 | NP_004170.1 |
| | Homo sapiens TPH2 | NP_775489.2 |
| | Gallus gallus | NP_990287.1 |
| | Mus musculus | NP_033440.1 |
| | Equus caballus | NP_001075252.1 |
| | Schistosoma mansoni | AAD01923.1 |
| 5HTP decarboxylase (EC 4.1.1.28) (ADDC) | Acidobacterium capsulatum | WP_015898075.1 |
| | Rattus norwegicus | XP_006251536.1 |
| | Sus scrofa | NP_999019.1 |
| | Homo sapiens | P20711-1, v2 |
| | Capsicum annuum | NP_001312016.1 |
| | Drosophila caribiana | AAM80956.1 |
| | Maricaulis maris (strain MCS10) | ABI65701.1 |
| | Oryza sativa subsp. Japonica | XP_015648768.1 |
| | Pseudomonas putida S16 | WP_013972057.1 |
| | Catharanthus roseus | P17770-1, v1 |
| | Candidatus Koribacter versatilis Ellin345 | ABF41161.1 |
| | Draconibacterium orientale | AHW60462.1 |
| | Verrucosispora maris | WP_013735011.1 |
| serotonin acetyltransferase (EC 2.3.1.87 or 2.3.1.5) (AANAT) | Streptomyces griseofuscus | AHL44344.1/ W8QGX9 (SEQ ID NO:1) |
| acetylserotonin O-methyltransferase (EC 2.1.1.4) (ASMT) | Homo sapiens | P46597-1, v1 |
| | Ocimum basilicum | Q9XGV9-1, v1 |
| | Bos taurus | P10950-1, v2 |
| | Takifugu rubripes | XP_011609423.1 |
| | Macaca mulatta | NP_001028112.1 |
| | Elephantulus edwardii | XP_006902482.1 |
| | Oryza sativa | XP_015610997.1 |
| | Rattus norvegicus | NP_653360.2 |
| | Gallus gallus | NP_990674.1 |
| | Chromobacterium violaceum | WP_011135808.1 |
| | Desulfotomaculum kuznetsovii DSM 6115 | YP_004515712.1 |
| | Xenopus (Silurana) tropicalis | NP_001011409.1 |
| | Pseudomonas fluorescens | WP_019095725.1 |
| | Candidatus Solibacter usitatus | WP_011682595.1 |
| | Fenneropenaeus chinensis | AAZ66373.1 |
| | Arabidopsis thaliana | NP_200227.1 |

Variants or homologs of any one or more of the enzymes and other proteins listed in Table 1, having the referenced activity and a sequence identity of at least 30%, such as at least 50%, such as at least 60%, such as at least 70%, such as at least 80%, such as at least 90%, such as at least 95%, such as at least 99%, over at least the catalytically active portion, optionally over the full length, of the reference amino acid sequence, are also contemplated. The variant or homolog may comprise, for example, 1, 2, 3, 4, 5 or more, such as up to 10 or more, amino acid substitutions, insertions or deletions as compared to the reference amino acid sequence. In particular conservative substitutions are considered. These are typically within the group of basic amino acids (histidine, lysine, arginine), acidic amino acids (glutamic acid and aspartic acid), polar amino acids (glutamine and asparagine), hydroxyl or sulphur-containing amino acids (serine, cysteine, threonine, and methionine), aromatic amino acids (phenylalanine, tryptophan and tyrosine), and aliphatic amino acids (glycine, alanine, valine, leucine, isoleucine). Amino acid substitutions which do not generally alter specific activity are known in the art and are described, for example, by H. Neurath and R. L. Hill, 1979, In: The Proteins, Academic Press, New York. The most commonly occurring exchanges are Ala to Ser, Val to Ile, Asp to Glu, Thr to Ser, Ala to Gly, Ala to Thr, Ser to Asn, Ala to Val, Ser to Gly, Tyr to Phe, Ala to Pro, Lys to Arg, Asp to Asn, Leu to Ile, Leu to Val, Ala to Glu, and Asp to Gly, and vice versa. Homologs, such as orthologs or paralogs, having the desired activity can be identified in the same or a related animal or microbial species using the reference sequences provided and appropriate activity testing. Specific enzyme variants are exemplified herein.

A nucleic acid sequence encoding an enzyme or other protein activity listed in Table 1 may encode an amino acid sequence that is homologous (i.e., native) or heterologous to the recombinant host cell in question.

Vectors

Also provided are vectors comprising nucleic acid sequences according to the above aspects and embodiments, e.g., encoding an sgAANAT variant and, optionally, one or more of a TPH, a 5HTP decarboxylase and an ASMT and/or enzymes for biosynthesizing or regenerating co-factors needed for these enzymes.

The specific design of the vector depends on, e.g., whether host cell already endogenously produces sufficient amounts of one or more of the enzymes or cofactors. Additionally, for transformation of a particular host cell, two or more vectors with different combinations of the enzymes used in the present invention can be applied. Accordingly, the nucleic acid sequences encoding the sgAANAT variant and the one or more additional enzymes may be located on the same vector, or on two or more different vectors. The vector can be a plasmid, phage vector, viral vector, episome, an artificial chromosome or other polynucleotide construct, and may, for example, include one or more selectable marker genes and appropriate expression control sequences.

Generally, regulatory control sequences are operably linked to the encoding nucleic acid sequences, and include constitutive, regulatory and inducible promoters, transcription enhancers, transcription terminators, and the like which are well known in the art. The encoding nucleic acid sequences can be operationally linked to one common expression control sequence or linked to different expression control sequences, such as one inducible promoter and one constitutive promoter.

The procedures used to ligate the various regulatory control and marker elements with the encoding nucleic acid sequences to construct the vectors of the present invention are well known to one skilled in the art (see, e.g., Sambrook et al., 2012, supra). In addition, methods have recently been developed for assembling of multiple overlapping DNA molecules (Gibson et al., 2008) (Gibson et al., 2009) (Li & Elledge, 2007), allowing, e.g., for the assembly multiple overlapping DNA fragments by the concerted action of an exonuclease, a DNA polymerase and a DNA ligase.

The promoter sequence is typically one that is recognized by the intended host cell. For an E. coli host cell, suitable promoters include, but are not limited to, the lac promoter, the T7 promoter, pBAD, the tet promoter, the Lac promoter, the Trc promoter, the Trp promoter, the recA promoter, the λ (lamda) promoter, and the PL promoter. Preferred promoters include the Trc promoter. For Streptomyces host cells, suitable promoters include that of Streptomyces coelicolor agarase (dagA). For a Bacillus host cell, suitable promoters include the sacB, amyL, amyM, amyQ, penP, xylA and xylB. Other promoters for bacterial cells include prokaryotic beta-lactamase (Villa-Kamaroff et al., 1978, Proceedings of the National Academy of Sciences USA 75: 3727-3731), and the tac promoter (DeBoer et al., 1983, Proceedings of the National Academy of Sciences USA 80: 21-25). For an S. cerevisiae host cell, useful promoters include the TEF1, HXT7, TDH3, ENO-1, GAL1, ADH1, ADH2, GAP, TPI, CUP1, PHOS and PGK, such as PGK1 promoters. Other useful promoters for yeast host cells are described by Romanos et al., 1992, Yeast 8: 423-488. Still other useful promoters for various host cells are described in "Useful proteins from recombinant bacteria" in Scientific American, 1980, 242: 74-94; and in Sambrook et al., 2012, supra.

In one embodiment, one or more or all of the exogenous nucleic acids is each under the control of a strong promoter, e.g., each separately selected from Trc, lac, lacUV5, Trp, T7, trac and PL promoter in an E. coli host cell, and each separately selected from PGK1, TEF1, HXT7 and TDH3 in an S. cerevisiae host cell.

A transcription terminator sequence is a sequence recognized by a host cell to terminate transcription, and is typically operably linked to the 3' terminus of an encoding nucleic acid sequence. Suitable terminator sequences for E. coli host cells include the T7 terminator region. Suitable terminator sequences for yeast host cells such as S. cerevisiae include CYC1, PGK, GAL, ADH, AOX1 and GAPDH. Other useful terminators for yeast host cells are described by Romanos et al., 1992, supra.

A leader sequence is a non-translated region of an mRNA which is important for translation by the host cell. The leader sequence is typically operably linked to the 5' terminus of a coding nucleic acid sequence. Suitable leaders for yeast host cells include S. cerevisiae ENO-1, PGK, alpha-factor, ADH2/GAP, TEF, and Kozak sequence.

A polyadenylation sequence is a sequence operably linked to the 3' terminus of a coding nucleic acid sequence which, when transcribed, is recognized by the host cell as a signal to add polyadenosine residues to transcribed mRNA. Useful polyadenylation sequences for yeast host cells are described by Guo and Sherman, 1995, Mol Cell Biol 15: 5983-5990.

A signal peptide sequence encodes an amino acid sequence linked to the amino terminus of an encoded amino acid sequence, and directs the encoded amino acid sequence into the cell's secretory pathway. In some cases, the 5' end of the coding nucleic acid sequence may inherently contain a signal peptide coding region naturally linked in translation reading frame, while a foreign signal peptide coding region may be required in other cases. Useful signal peptides for yeast host cells can be obtained from the genes for S. cerevisiae alpha-factor and invertase. Other useful signal peptide coding regions are described by Romanos et al., 1992, supra. An exemplary signal peptide for an *E. coli* host cell can be obtained from alkaline phosphatase. For a *Bacillus* host cell, suitable signal peptide sequences can be obtained from alpha-amylase and subtilisin. Further signal peptides are described by Simonen and Palva, 1993, Microbiological Reviews 57: 109-137.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tec, and tip operator systems. For example, one or more promoter sequences can be under the control of an IPTG inducer, initiating expression of the gene once IPTG is added. In yeast, the ADH2 system or GAL1 system may be used. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the respective encoding nucleic acid sequence would be operably linked with the regulatory sequence.

The choice of the vector will typically depend on the compatibility of the vector with the host cell into which the vector is to be introduced. The vectors may be linear or closed circular plasmids. The vector may also be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon, may be used.

The vectors of the present invention preferably contain one or more selectable markers which permit easy selection of transformed cells. The selectable marker genes can, for example, provide resistance to antibiotics or toxins, complement auxotrophic deficiencies, or supply critical nutrients not in the culture media, and/or provide for control of chromosomal integration. Examples of bacterial selectable markers are the dal genes from *Bacillus subtilis* or *Bacillus licheniformis*, or markers which confer antibiotic resistance such as ampicillin, kanamycin, chloramphenicol, or tetracycline resistance. Suitable markers for yeast host cells are ADE2, HIS3, LEU2, LYS2, MET3, TRP1, and URA3.

The vectors of the present invention may also contain one or more elements that permit integration of the vector into the host cell genome or autonomous replication of the vector in the cell independent of the genome. For integration into the host cell genome, the vector may rely on an encoding nucleic acid sequence or other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. The integrational elements may, for example, non-encoding or encoding nucleotide sequences. The vector may be integrated into the genome of the host cell by non-homologous recombination. For example, for integration into an *E. coli* chromosome, the vector may contain elements directing integration of the nucleic acid sequences at lambda red recombination or the Tn7 site-specific integration method according to McKenzie G and Nancy L C (2006).

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo. Examples of bacterial origins of replication are the origins of replication of plasmids pBR322, pUC19, pACYC177, and pACYC184 permitting replication in *E. coli*, and pUB1 10, pE194, pTA1060, and pAMβi permitting replication in *Bacillus*. Examples of origins of replication for use in a yeast host cell are the 2 micron origin of replication, ARS1, ARS4, the combination of ARS1 and CEN3, and the combination of ARS4 and CEN6.

More than one copy of the nucleic acid sequence encoding the enzyme or protein of interest may be inserted into the host cell to increase production of the gene product. An increase in the copy number of the encoding nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the sequence, can be selected for by cultivating the cells in the presence of the appropriate selectable agent.

Recombinant Host Cells

Recombinant host cells expressing sgAANAT or a catalytically active fragment or variant thereof, optionally from the above-described nucleic acid sequences or vectors, are also provided. Suitable host cells for expressing ASMT variants include, for example, mammalian and microbial cells. Once expressed, the AANAT variants can, optionally, be retrieved and purified from the host cells or the cell medium in which the host cells are grown.

The recombinant host cell can also be capable of producing serotonin or melatonin. For example, mammalian cells comprising a native biosynthetic pathway for serotonin and/or melatonin can be transformed with a vector comprising a nucleic acid sequence encoding sgAANAT or a catalytically active fragment or variant thereof, under the control of a promoter suitable for the selected mammalian host cell and/or linked to elements that promote integration of the nucleic acid sequence into the host cell genome. Alternatively, the recombinant host cell of the invention can be prepared from any host cell by introducing heterologous or overexpressing endogenous enzymes of the necessary biometabolic pathways, using recombinant techniques well known in the art and cited elsewhere herein.

The host cell is preferably tryptophan autotrophic (i.e., capable of endogenous biosynthesis of L-tryptophan), grows on synthetic medium with suitable carbon sources, and expresses a suitable RNA polymerase (such as, e.g., T7 polymerase). In all known microorganisms, tryptophan production takes place via a single metabolic pathway (Somerville, R. L., Herrmann, R. M., 1983, Amino acids, Biosynthesis and Genetic Regulation, Addison-Wesley Publishing Company, U.S.A.: 301-322 and 351-378; Aida et al., 1986, Bio-technology of amino acid production, progress in industrial microbiology, Vol. 24, Elsevier Science Publishers, Amsterdam: 188-206). Tryptophan can also or alternatively be added to the medium of a recombinant host cell comprising sgAANAT or a catalytically active fragment or variant thereof, as well as TPH, DDC, ASMT and other enzymes providing for a melatonin biosynthetic pathway.

The recombinant host cell is typically capable of biosynthesizing and/or regenerating the cofactors used by the enzymes in the melatonin biosynthesis pathway. In particular, the recombinant host cell is preferably capable of biosynthesizing, regenerating, or biosynthesizing and regenerating, one or more cofactors for TPH, AANAT and ASMT (FIG. 1).

To provide cofactor for TPH-catalyzed hydroxylation of tryptophan, the recombinant host cell is preferably capable of biosynthesizing one or both of THB and MH4 via endogenous or heterologous (introduced) pathways. For example, endogenous pathways for THB biosynthesis are present in mammalian cells. Microbial cells generally do not biosynthesize THB endogenously, but it has been reported that the endogenous compound MH4 may substitute for or replace THB as cofactor for TPH in such cells (US 2014/134689 AA; University of California). GTP cyclohydrolase I (such as, e.g. FolE)-catalyzed pterin biosynthesis resulting in MH4 takes place in many organisms including both prokaryotes and eukaryotes (see, e.g. FIG. 9 of US 2014/134689 AA). So, for example, in one embodiment, the microbial host cell is an *E. coli* cell comprising the endogenous enzymes folE, folX, P-ase, and folM, optionally upregulated or expressed from one or more endogenous vectors. Useful FolE variants are described in, e.g., WO 2017/167866.

Alternatively, enzymes of biosynthetic pathways for producing and/or regenerating THB can be introduced recombinantly, as described in WO 2013/127914 A1, WO 2013/127915 A1 and WO 2015/032911 A1 (Danmarks Tekniske Universitet) and in US 2014/134689 AA (University of California), all of which hereby incorporated by reference in their entireties. Briefly, in one embodiment, the recombinant cell comprises an exogenous pathway producing THB from GTP and herein referred to as "first THB pathway", comprising a GTP cyclohydrolase I (GCH1), a 6-pyruvoyl-tetrahydropterin synthase (PTPS), and a sepiapterin reductase (SPR) (see FIG. 1). The addition of such a pathway to microbial cells such as *E. coli* (JM101 strain), *S. cerevisiae* (KA31 strain) and *Bacillus subtilis* (1A1 strain (TrpC2)) has also been described in, e.g., U.S. Pat. No. 7,807,421. In one embodiment, the recombinant cell comprises a pathway producing THB by regenerating THB from HTHB, herein referred to as "second THB pathway", comprising a 4a-hydroxytetrahydrobiopterin dehydratase (PCBD1) and a 6-pyruvoyl-tetrahydropterin synthase (DHPR). As shown in FIG. 1, the second THB pathway converts the HTHB formed by the L-tryptophan hydroxylase-catalyzed hydroxylation of L-tryptophan back to THB, thus allowing for a more cost-efficient 5HTP synthesis. In one embodiment, the recombinant host cell comprises enzymes of both the first and second THB pathways. Non-limiting and exemplary nucleic acids encoding enzymes of the first and second THB pathways for use in aspects and embodiments of the present invention include those shown in Table 1 of WO 2015/032911 A1, which is hereby specifically incorporated by reference, including the actual amino acid sequences referred to in the table as SEQ ID numbers.

Most types of host cells (e.g., mammalian host cells, yeast host cells such as *S. cerevisiae*, bacteria such as *E. coli*, etc.) are capable of producing and regenerating acetyl-CoA and SAM; the cofactors for AANAT and ASMT, respectively.

AcCoA serves as a metabolic cofactor in the AANAT reaction, but is also part of other, endogenous pathways in, e.g., microbial cells.

SAM is a principal methyl donor in various intracellular transmethylation reactions. It is synthesized in the cell through SAM synthetase from methionine and ATP, and natively generated through the SAM cycle, which consists of a methyl transferase, an S-adenosyl-L-homocysteine hydrolase, a folate transferase, and an S-adenosyl-methionine synthetase (Lee et al., Korean J. Chem. Eng. 2010, 27, 587-589). Accordingly, in the ASMT-catalyzed, last reaction in the production of melatonin from L-tryptophan, N-acetylserotonin and SAM are converted to melatonin and SAH. SAH can then be recycled back to SAM via the SAM-cycle in microbial cells where the S-adenosyl-L-methionine cycle is native (or exogenously added) and constitutively expressed, such as, e.g., in *E. coli*. The enzymes of such native pathways can also, in needed, be upregulated or expressed from an exogenously introduced vector, using well-known recombinant techniques known in text books referenced elsewhere herein. Non-limiting and exemplary nucleic acids encoding enzymes of the SAM cycle for use in aspects and embodiments of the present invention include those shown in Table 1 of WO 2015/032911 A1, which is hereby specifically incorporated by reference, including the actual amino acid sequences referred to in the table as SEQ ID numbers.

The recombinant host cell is typically prepared by introducing into the host cell, typically via transformation, one or more vectors according to any preceding embodiment, using standard methods known in the art and cited elsewhere herein. The introduction of a vector into a bacterial host cell may, for instance, be effected by protoplast transformation (see, e.g., Chang and Cohen, 1979, Molecular General Genetics 168: 111-115), using competent cells (see, e.g., Young and Spizizen, 1961, Journal of Bacteriology 81: 823-829, or Dubnau and Davidoff-Abelson, 1971, Journal of Molecular Biology 56: 209-221), electroporation (see, e.g., Shigekawa and Dower, 1988, Biotechniques 6: 742-751), or conjugation (see, e.g., Koehler and Thorne, 1987, Journal of Bacteriology 169: 5771-5278).

As described above, the vector, once introduced, may be maintained as a chromosomal integrant or as a self-replicating extra-chromosomal vector.

Preferably, for transformation of an *E. coli* or other bacterial host cell, the vectors are designed as follows: A Ptrc promoter is used to control the expressions of a gene or an artificial operon containing up to three genes connected with a linker sequence, in order to express the genes at a suitable level so that the introduction of heterologous genes/pathways do not overdraw substrates or energy in the host cell. In one particular embodiment, the recombinant microbial cell, preferably derived from a bacterial cell, is transformed according to a strategy outlined in the Examples.

Preferably, for transformation of a yeast host cell such as *S. cerevisiae*, the heterologous genes are integrated onto chromosome using a homologous recombination based method (Mikkelsen et al., 2012). As compared with gene expression based on plasmids, the chromosomally integrated genes can be expressed with higher fidelity and resulted in better protein translation, in particular for multiple gene co-expression systems.

The transformation can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product, including those referred to above and relating to measurement of 5HTP production. Expression levels can further be optimized to obtain sufficient expression using methods well known in the art and as disclosed herein.

In a preferred embodiment, the host cell is a microbial cell. The microbial host cell for use in the present invention is typically unicellular and can be, for example, a bacterial cell, a yeast host cell, a filamentous fungal cell, or an algeal cell. Examples of suitable host cell genera include, but are not limited to, *Acinetobacter, Agrobacterium, Alcaligenes, Anabaena, Aspergillus, Bacillus, Bifidobacterium, Brevibacterium, Candida, Chlorobium, Chromatium, Corynebacteria, Cytophaga, Deinococcus, Enterococcus, Erwinia, Erythrobacter, Escherichia, Flavobacterium, Hansenula, Klebsiella, Lactobacillus, Methanobacterium, Methylobacter, Methylococcus, Methylocystis, Methylomicrobium, Methylomonas, Methylosinus, Mycobacterium, Myxococcus, Pantoea, Phaffia, Pichia, Pseudomonas, Rhodobacter, Rhodococcus, Saccharomyces, Salmonella, Sphingomonas, Streptococcus, Streptomyces, Synechococcus, Synechocystis, Thiobacillus, Trichoderma, Yarrowia* and *Zymomonas*.

In one embodiment, the host cell is bacterial cell, e.g., an *Escherichia* cell such as an *Escherichia coli* cell; a *Bacillus* cell such as a *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* or a *Bacillus thuringiensis* cell; or a *Streptomyces* cell such as a *Streptomyces lividans* or *Streptomyces murinus* cell. In a particular embodiment, the recombinant microbial cell is derived from cell of the *Escherichia* genus, such as an *Escherichia coli* cell. In another particular embodiment, the host cell is of an *E. coli* strain selected from the group consisting of K12.DH1 (Proc. Natl. Acad. Sci. USA, volume 60, 160 (1968)), JM101, JM103 (Nucleic Acids Research (1981), 9, 309), JA221 (J. Mol. Biol. (1978), 120, 517), HB101 (J. Mol. Biol. (1969), 41, 459) and C600 (Genetics, (1954), 39, 440).

In one embodiment, the host cell is a fungal cell, such as, e.g., a yeast cell. Exemplary yeast cells include *Candida, Hansenula, Kluyveromyces, Pichia, Saccharomyces, Schizosaccharomyces* and *Yarrowia* cells. In a particular embodiment, the host cell is an *S. cerevisiae* cell. In another particular embodiment, the host cell is of an *S. cerevisie* strain selected from the group consisting of *S. cerevisiae* KA31, AH22, AH22R-, NA87-11A, DKD-5D and 20B-12, *S. pombe* NCYC1913 and NCYC2036 and *Pichia pastoris* KM71.

In one embodiment, the recombinant microbial is derived from an *Escherichia, Saccharomyces*, a *Schizosaccharomyces*, a *Corynebacterium*, a *Bacillus* or a *Streptomyces* cell. In one embodiment, the recombinant microbial is derived from an *Escherichia coli* or *Saccharomyces cerevisiae* cell.

Production of N-Acetylserotonin or Melatonin

The invention also provides a method of producing N-acetylserotonin or melatonin, comprising culturing the recombinant microbial cell of any preceding aspect or embodiment in a medium comprising a carbon source. The desired compound can then optionally be isolated or retrieved from the medium, and optionally further purified.

Also provided is a method of preparing a composition comprising N-acetylserotonin or melatonin, comprising culturing the recombinant microbial cell of any preceding aspect or embodiment, isolating and purifying the compound, and adding any excipients to obtain the composition.

Suitable carbon sources include carbohydrates such as monosaccharides, oligosaccharides and polysaccharides. As used herein, "monosaccharide" denotes a single unit of the general chemical formula $Cx(H_2O)y$, without glycosidic connection to other such units, and includes glucose, fructose, xylose, arabinose, galactose and mannose. "Oligosaccharides" are compounds in which monosaccharide units are joined by glycosidic linkages, and include sucrose and lactose. According to the number of units, oligosacchardies are called disaccharides, trisaccharides, tetrasaccharides, pentasaccharides etc. The borderline with polysaccharides cannot be drawn strictly; however the term "oligosaccharide" is commonly used to refer to a defined structure as opposed to a polymer of unspecified length or a homologous mixture. "Polysaccharides" is the name given to a macromolecule consisting of a large number of monosaccharide residues joined to each other by glycosidic linkages, and includes starch, lignocellulose, cellulose, hemicellulose, glycogen, xylan, glucuronoxylan, arabinoxylan, arabinogalactan, glucomannan, xyloglucan, and galactomannan. Other suitable carbon sources include acetate, glycerol, pyruvate and gluconate. In one embodiment, the carbon source is selected from the group consisting of glucose, fructose, sucrose, xylose, mannose, galactose, rhamnose, arabinose, fatty acids, glycerine, glycerol, acetate, pyruvate, gluconate, starch, glycogen, amylopectin, amylose, cellulose, cellulose acetate, cellulose nitrate, hemicellulose, xylan, glucuronoxylan, arabinoxylan, glucomannan, xyloglucan, lignin, and lignocellulose. In one embodiment, the carbon source comprises one or more of lignocellulose and glycerol. In one embodiment, the carbon source is a simple carbon source such as glucose, xylose, fructose, arabinose, galactose, mannose, glycerol, acetate, or a mixture of any thereof.

The culture conditions are adapted to the recombinant microbial host cell, and can be optimized to maximize production of N-acetylserotonin or melatonin or a related compound by varying culture conditions and media components as is well-known in the art.

For a recombinant *Escherichia coli* cell, exemplary media include LB medium and M9 medium (Miller, Journal of Experiments in Molecular Genetics, 431-433, Cold Spring Harbor Laboratory, New York, 1972), optionally supplemented with one or more amino acids. When an inducible promoter is used, the inductor can also be added to the medium. Examples include the lac promoter, which can be activated by adding isopropyl-beta-thiogalacto-pyranoside (IPTG) and the GAL/BAD promoter, in which case galactose/arabinose can be added. The culturing can be carried out a temperature of about 10 to 40° C. for about 3 to 72 hours, if desired, with aeration or stirring.

For a recombinant *Bacillus* cell, culturing can be carried out in a known medium at about 30 to 40° C. for about 6 to 40 hours, if desired with aeration and stirring. With regard to the medium, known ones may be used. For example, pre-culture can be carried out in an LB medium and then the main culture using an NU medium.

For a recombinant yeast cell, Burkholder minimum medium (Bostian, K. L., et al. Proc. Natl. Acad. Sci. USA, volume 77, 4505 (1980)), SD medium containing 0.5% of Casamino acid (Bitter, G. A., et al., Proc. Natl. Acad. Sci. USA, volume 81, 5330 (1984), and Delft medium (Verduyn et al., Yeast 1992, 8, 501-517) can be used. The pH is preferably adjusted to about 5-8. For example, a synthetic medium may contain, per litre: (NH4)2SO4, 5 g; KH2PO4, 3 g; MgSO4.7H2O, 0.5 g; EDTA, 15 mg; ZnSO4.7H2O, 4.5 mg; CoCl2.6H2O, 0.3 mg; MnCl2.4H2O, 1 mg; CuSO4 5H2O, 0.3 mg; CaCl2.2H2O, 4.5 mg; FeSO4.7H2O, 3 mg; NaMoO4.2H2O, 0.4 mg; H3BO3, 1 mg-KI, 0.1 mg; and 0.025 ml silicone antifoam(BDH). Filter-sterilized vitamins can be added after heat sterilization (120° C.), to final concentrations per litre of: biotin, 0.05 mg; calcium pantothenate, 1 mg; nicotinic acid, 1 mg; inositol, 25 mg; thiamine HCl, 1 mg; pyridoxine HCl, 1 mg; and para-aminobenzoic acid, 0.2 mg. The medium can then be adjusted to pH6 with KOH. Culturing is preferably carried out at about 20 to about 40° C., for about 24 to 84 hours, if desired with aeration or stirring.

In one embodiment, no L-tryptophan is added to the medium. In another embodiment, no L-tryptophan or THB is added to the medium, so that the production of melatonin or its precursors or related compounds rely on substrates biosynthesized in the recombinant host cell.

Isolation of the desired product from the cell culture can be achieved, e.g., by separating the compound from the cells using a membrane, using, for example, centrifugation or filtration methods. The product-containing supernatant is then collected. Further purification of the desired compound can then be carried out using known methods, such as, e.g., salting out and solvent precipitation; molecular-weight-based separation methods such as dialysis, ultrafiltration, and gel filtration; charge-based separation methods such as ion-exchange chromatography; and methods based on differences in hydrophobicity, such as reversed-phase HPLC; and the like. In one embodiment, ion-exchange chromatography is used for purification of serotonin. In one embodiment, reverse-phase chromatography is used for separation and/or purification of melatonin. An exemplary method for purification of these indolamines using reversed-phase chromatography is described in Harumi et al., (1996) (J Chromatogr B 675:152-156).

Once a sufficiently pure preparation has been achieved, suitable excipients, stabilizers can optionally be added and the resulting preparation incorporated in a composition for use in preparing a product such as, e.g., a dietary supplement, a pharmaceutical, a cosmeceutical, or a nutraceutical. For a dietary supplement comprising melatonin, each serving can contain, e.g., from about 0.01 mg to about 100 mg melatonin, such as from about 0.1 mg to about 10 mg, or about 1-5 mg, such as 2-3 mg. Emulsifiers may be added for stability of the final product. Examples of suitable emulsifiers include, but are not limited to, lecithin (e.g., from egg or soy), and/or mono- and di-glycerides. Other emulsifiers are readily apparent to the skilled artisan and selection of suitable emulsifier(s) will depend, in part, upon the formulation and final product. Preservatives may also be added to the nutritional supplement to extend product shelf life. Preferably, preservatives such as potassium sorbate, sodium sorbate, potassium benzoate, sodium benzoate or calcium disodium EDTA are used.

Example 1

Media and Growth Conditions

All strains were maintained at 37° C. in LB (Lennox) Broth (Sigma-Aldrich), 2xYT or M9 minimum media containing 1xM9 minimal salts (BD Difco™), 2 mM MgSO$_4$, 100 µM CaCl$_2$, 500-fold diluted trace minerals (10 g/l FeCl$_3$.6H$_2$O, 2 g/l ZnSO$_4$.7H$_2$O, 0.4 g/l CuCl$_2$.2H$_2$O, 1 g/l MnSO$_4$.H$_2$O, 0.6 g/l CoCl$_2$.6H$_2$O, and 1.6 mM EDTA, pH 8.0), 1xATCC® Vitamin Supplement (ATCC MD-VS™), and 0.2% glucose (w/v). When added, kanamycin, spectinomycin, and chloramphenicol was at 25, 50 and 25 mg/l, respectively.

Strains

All strains used in this study were derived from BW25113. When required, genomic modification was achieved by means of either lambda red recombination or a Tn7 site-specific integration method (McKenzie G and Nancy L C, 2006)).

Time-Course Screening

All time-course screening was set up using M9 medium supplemented with 100-200 mg/l of serotonin. Cultivation was taken place in 24 deep-well plates at 37° C. and samples were withdrawn periodically for metabolites analysis as described below.

Metabolite Analysis by LC-MS

LC-MS data was collected on OrbiTrap Fusion High Resolution Mass Spectrometer system coupled with an Ultimate 3000 UHPLC pump (Thermo, San Jose, Calif.). Samples were held in the autosampler at a temperature of 10.0° C. during the analysis. 1 µL Injections of the sample were made onto a Thermo HyperSil Gold PFP HPLC column, with a 3 um particle size, 2.1 mm i.d. and 150 mm long. The column was held at a temperature of 35.0° C. The solvent system used was Solvent A "Water with 0.1% formic acid" and Solvent B "Acetonitrile with 0.1% formic". The Flow Rate was 1.000 ml/min with an Initial Solvent composition of % A=95, % B=5 held until 0.50 min, the solvent composition was then changed following a Linear Gradient until it reached % A=70.0 and % B=30.0 at 1.50 min. The solvent composition was then changed following a Linear Gradient until it reached % A=5.0 and % B=95.0 at 2.00 min This was held until 2.50 min when the solvent was returned to the initial conditions and the column was re-equilibrated until 3.00 min. The first 0.25 min of the run was diverted to waste using the divert valve, following which the column eluent flowed directly into the Heated ESI probe of the MS which was held at 325° C. and a voltage of 3500 V. Data was collected in positive ion mode over the mass range 50 to 1000 m/z at a resolution of 15.000. The other MS settings were as follows, Sheath Gas Flow Rate of 60 units, Cone Gas Flow Rate of 20 units Cone Temp was 275° C.

Comparison of AANATs

Five AANAT gene candidates were initially selected to test their activity in *E. coli*: AANAT from *Bos taurus* (SEQ ID NO:2), *Gallus gallus* (SEQ ID NO:3), *Oryctolagus cuniculus* (SEQ ID NO:4), *Homo sapiens* (SEQ ID NO:6) and *Streptomyces griseofuscus* (SEQ ID NO:1). All AANAT genes were able to produce acetylserotonin from serotonin when expressed from a plasmid of ColE1 origin and a Trc promoter (Table 2). This observation concluded their active expression in *E. coli*.

TABLE 2

Production of acetylserotonin from serotonin by various AANAT genes expressed from plasmids

| Origin of AANAT gene | Extra-cellular serotonin mg/l | Extra-cellular acetylserotonin mg/l |
|---|---|---|
| *Bos taurus* | 60 | 154 |
| *Gallus gallus* | 70 | 161 |

TABLE 2-continued

Production of acetylserotonin from serotonin by various AANAT genes expressed from plasmids

| Origin of AANAT gene | Extra-cellular serotonin mg/l | Extra-cellular acetylserotonin mg/l |
|---|---|---|
| Oryctolagus cuniculus | 80 | 158 |
| Homo sapiens | 117 | 114 |
| Streptomyces griseofuscus | 114 | 170 |
| Medium blank | 250 | 0 | all AANAT genes were expressed from a plasmid of ColE1 origin under the control of a Trc promoter.

Figure 2:
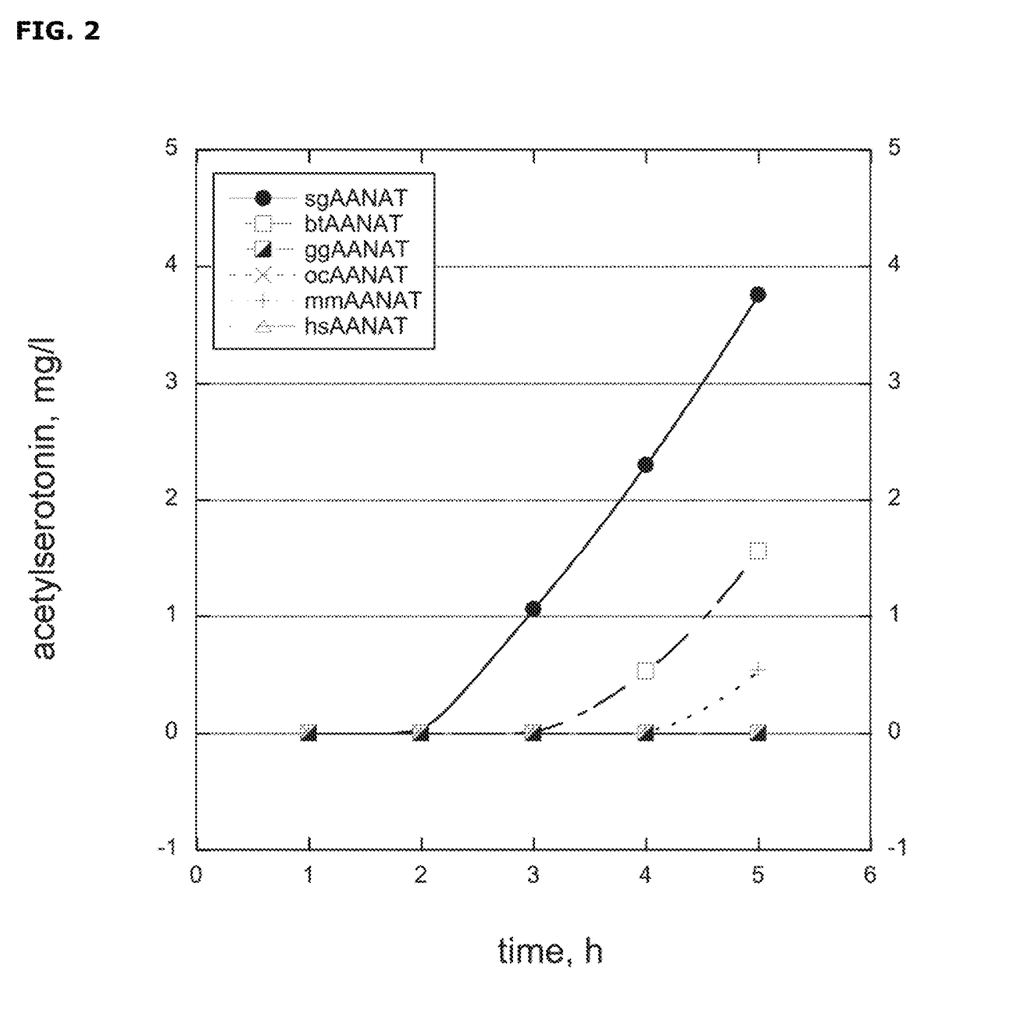
FIG. 2: N-acetylserotonin production profile of six AANATs with serotonin feeding in vivo in M9 medium. The AANATs were expressed from chromosomally integrated genes. btAANAT (*Bos taurus*), ggAANAT (*Gallus gallus*), ocAANAT (*Oryctolagus cuniculus*), mmAANAT (*Mus musculus*), hsAANAT (*Homo sapiens*) and sgAANAT (*Streptomyces griseofuscus*).

To further evaluate their activities, all five genes as well as a gene encoding Mus musculus AANAT (SEQ ID NO:5) were chromosomally integrated as a single copy at the Tn7 site. As revealed in FIG. 2, the sgAANAT gene from Streptomyces griseofuscus showed the highest activity following by btAANAT and mmAANAT from Bos taurus and Mus musculus, respectively.

sgAANAT Variant

Figure 3:
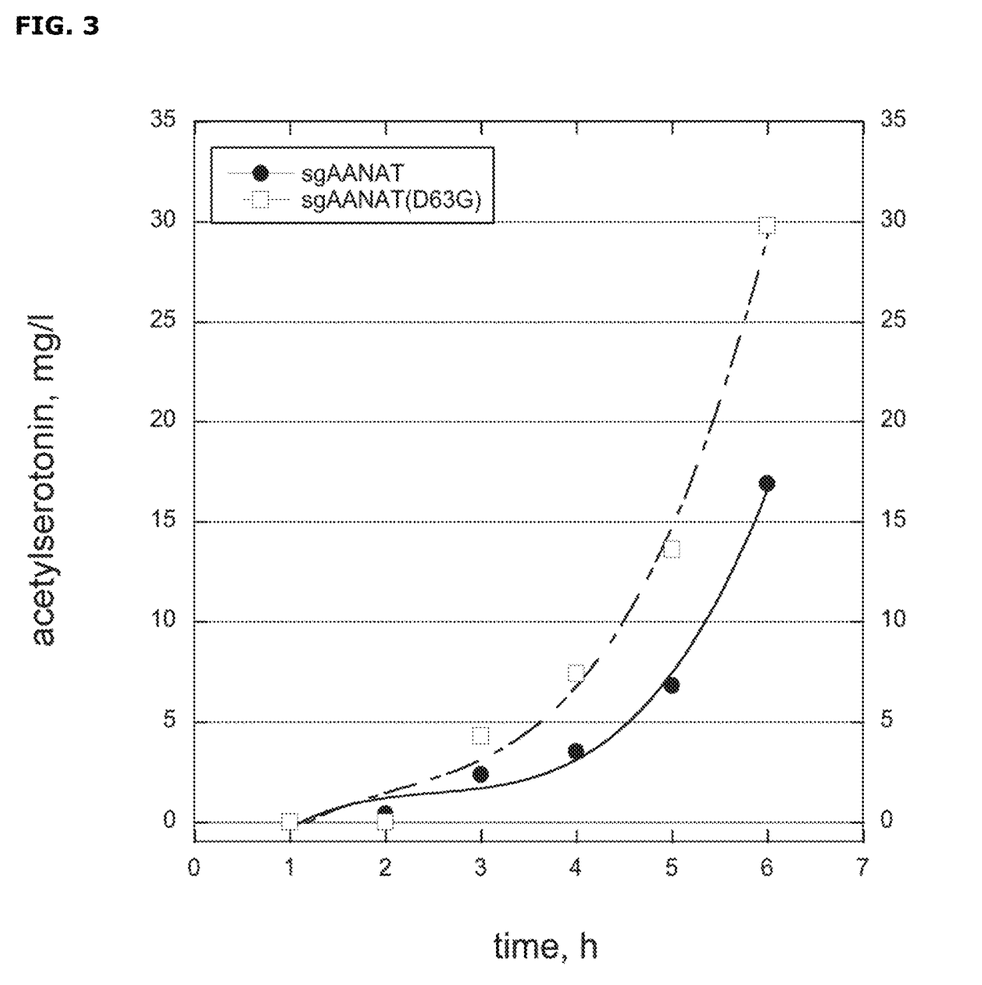
FIG. 3: Comparison between wild type and mutant (D63G) sgAANAT with serotonin feeding in vivo in M9 medium.

A D63G mutation of sgAANAT was identified in a screening method. Subsequently, its mutational effect was compared to wild type by introducing a single copy of the respective DNA sequence into the chromosome. As shown in FIG. 3, the sgAANAT(D63G) variant outperformed the wild-type version and the acetylserotonin yield was increased by approximately two-fold; 35.3 mg/g CDW vs 14.6 mg/g CDW.

Example 2

This Example shows that sgAANAT(D63G) improves melatonin formation in fermentation conditions.

The HMP1489 strain was compared to HMP626 in melatonin production under fermentation conditions. The HMP1489 cells genotypically resembled to HMP626 except HMP1489 only had one copy of sgAANAT(D63G) gene on the E. coli chromosome while wild-type sgAANAT was expressed from a medium copy number plasmid in HMP626.

The fermentation was carried out at 30° C. and pH6 in 1 L glass fermenters (Sartorius, Germany). Initial airflow rate was 0.4 L min−1 and initial stirrer speed 800 rpm. pH control was achieved by addition of 15% $NH_4OH$. The minimal batch medium (400 mL) contained 20 gL−1 glucose, the feeding solution (400 mL) 360 gL−1 glucose and 15 gL−1 tryptophan. After completion of the batch phase the stirrer speed was increased to 1000 rpm and an exponential glucose limited feed was applied with an exponential coefficient of 0.055 h-1. DO was kept above 40% by sparging pure oxygen if required.

The batch medium consisted of (gL−1): $(NH_4)_2SO_4$, 10; $KH_2PO_4$, 14; glucose, 20; $ZnCl_2$, 0.1; $FeSO_4*7H_2O$, 0.15; $Na_3$-citrate, 1.5; $MgSO_4*7H_2O$, 0.49; $CaCl_2*2H_2O$, 0.01; $AlK(SO_4)_2*12H_2O$, 0.003; $CoSO_4*7H_2O$, 0.001; $CuSO_4*5H_2O$, 0.003; $H_3BO_3$, 0.001; $MnSO_4*H_2O$, 0.024; $Na_2MoO_4*2H_2O$, 0.003; $NiSO_4*6H_2O$, 0.003; $ZnSO_4*7H_2O$, 0.015. The following vitamins were added (µgL−1): pyridoxine HCl, 10; thiamine HCl, 5; riboflavin, 5; nicotinic acid, 5; Ca-D-(+)phantothenate, 5; p-aminobenzoic acid, 5; thiotic acid, 5; biotin, 2; folic acid, 2; vitamin B12, 0.1.

The feed solution consisted of (gL−1): $KH_2PO_4$, 14; glucose, 360; L-tryptophan, 15; $ZnCl_2$, 0.1; $FeSO_4*7H_2O$, 0.15; $Na_3$-citrate, 1.5; $MgSO_4*7H_2O$, 18; $CaCl_2*2H_2O$, 0.01; $AlK(SO_4)_2*12H_2O$, 0.009; $CoSO_4*7H_2O$, 0.003; $CuSO_4*5H_2O$, 0.008; $H_3BO_3$, 0.002; $MnSO_4*H_2O$, 0.072; $Na_2MoO_4*2H_2O$, 0.009; $NiSO_4*6H_2O$, 0.008; $ZnSO_4*7H_2O$, 0.045. The following vitamins were added (µgL−1): pyridoxine HCl, 30; thiamine HCl, 15; riboflavin, 15; nicotinic acid, 15; Ca-D-(+)phantothenate, 15; p-aminobenzoic acid, 15; thiotic acid, 15; biotin, 6; folic acid, 6; vitamin B12, 0.3.

Figure 4:
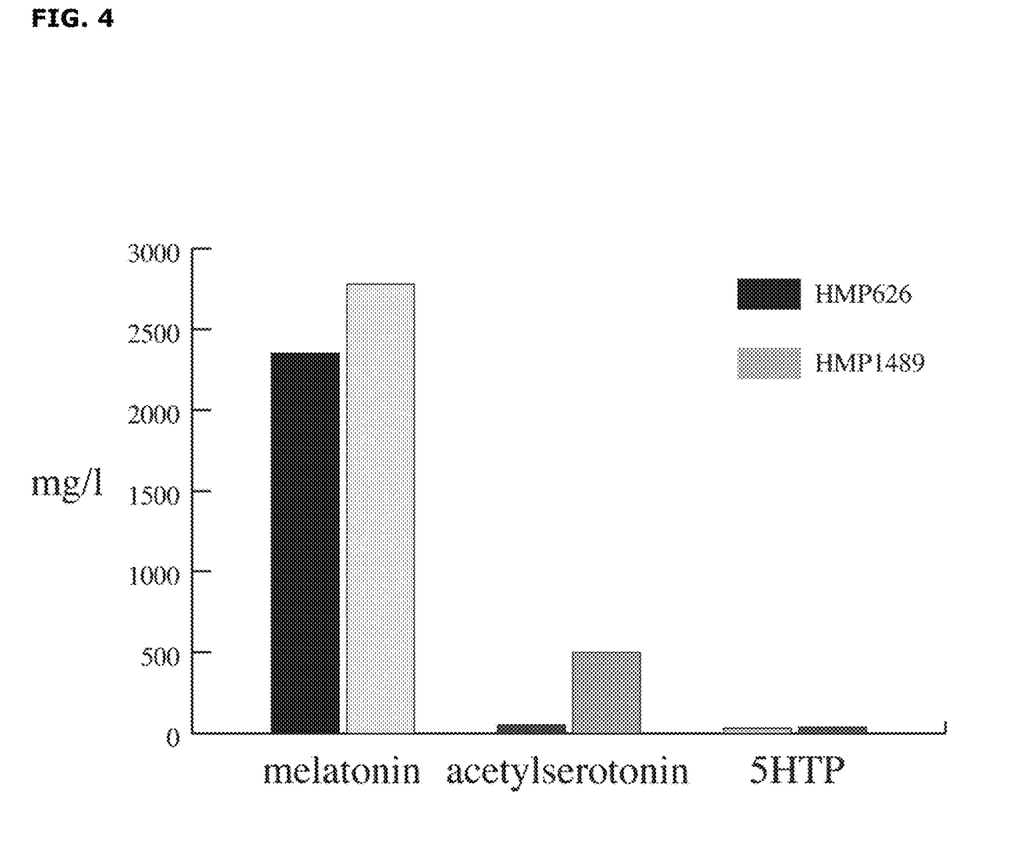
FIG. 4: Melatonin production in 1 L fermentation using either wild type sgAANAT or sgAANAT(D63G).

As shown in FIG. 4, HMP626 produced 2.3±0.1 g/l of melatonin while HMP1489 produced 2.8±0.1 g/l, representing a 20% increase in melatonin titre. In addition, a significant amount of acetylserotonin accumulation was observed in HMP1489 at 0.5±0.1 g/l that was approximately 10-fold more of HMP626. There were only trace amounts of 5HTP observed and no serotonin accumulation. Overall, these results together indicated that the higher turnover rate of the sgAANAT(D63G) variant was beneficial in melatonin formation by favouring synthesis of acetylserotonin, which is the precursor of melatonin.

LIST OF REFERENCES

Klein et al. (2007), The Journal Of Biological Chemistry Vol. 282, No. 7, pp. 4233-4237,
Liu et al., Angew Chem 2014; 53:136-139
McKenzie G and Nancy L C (2006) BMC Microbiol 6:39
Thomas et al., Analytical Biochemistry 1990; 184:228-34.
WO 2013/127915 A1 (Danmarks Tekniske Universitet)
WO 2015/032911 A1 (Danmarks Tekniske Universitet)
US 2014/134689 AA (University of California)
WO 2017/167866 (Danmarks Tekniske Universitet)
WO 2017/202897 (Danmarks Tekniske Universitet)
EP 0 456 507 A2 (Eli Lilly & Co.)
UNIPROT ref. XONDI9_STRA9

The invention claimed is:

1. A catalytically active variant of arylalkylamine N-acetyltransferase (AANAT) from *Streptomyces griseofuscus* (SEQ ID NO:1), the variant AANAT having at least 85% sequence identity to SEQ ID NO:1, comprising a mutation in residue D63 and providing for an increased yield in vivo of N-acetylserotonin from serotonin relative to native enzyme.

2. The catalytically active variant of claim 1, wherein the D63 mutation is an amino acid substitution selected from D63G, D63A, D63V, D63L and D63I.

3. A catalytically active variant of AANAT from *Streptomyces griseofuscus* (SEQ ID NO:1), wherein the variant AANAT comprises SEQ ID NO:1 and has a D63G amino acid substitution.

4. A nucleic acid sequence encoding the catalytically active variant of claim 1.

5. A vector comprising the nucleic acid sequence of claim 4, optionally further comprising elements that promote integration of the nucleic acid sequence into the host cell genome.

6. A recombinant host cell comprising the nucleic acid sequence of claim 4.

7. The recombinant host cell of claim 6, wherein the nucleic acid sequence is chromosomally integrated.

8. The recombinant host cell of claim 6, which is derived from a mammalian cell, a bacterial cell, a yeast cell, a filamentous fungal cell or an algal cell.

9. The recombinant host cell of claim 8, which is derived from an *Escherichia* cell or an *S. cerevisiae* cell.

10. A recombinant host cell which is derived from an *E. coli* or *S. cerevisiae* cell, comprising a chromosomally integrated gene encoding an AANAT having at least 85% identity to SEQ ID NO: 1 from *Streptomyces griseofuscus* or a catalytically active fragment or variant thereof, wherein said AANAT or catalytically active fragment thereof comprises a D63 amino acid substitution.

11. The recombinant host cell of claim 10, wherein the AANAT or catalytically active fragment thereof comprises a D63G amino acid substitution.

12. The recombinant host cell of claim 6, comprising a native or heterologous biosynthetic pathway for producing serotonin and, optionally, an acetylserotonin O-methyltransferase (ASMT).

13. A method of producing N-acetylserotonin, comprising culturing the recombinant host cell of claim 12 in a medium comprising a carbon source, and, optionally, isolating N-acetyl serotonin.

14. A method of producing melatonin, comprising culturing the recombinant host cell of claim 12 in a medium comprising a carbon source, and, optionally, isolating melatonin, wherein the recombinant host cell comprises an ASMT.

15. A process for preparing the recombinant host cell of claim 6, comprising transforming a host cell with the vector of claim 5.

16. A nucleic acid sequence encoding the catalytically active variant of claim 3.

17. A recombinant host cell comprising the nucleic acid sequence of claim 16.

18. The recombinant host cell of claim 17, wherein the nucleic acid sequence is chromosomally integrated.

19. The recombinant host cell of claim 17, which is derived from a mammalian cell, a bacterial cell, a yeast cell, a filamentous fungal cell or an algal cell.

20. The recombinant host cell of claim 19, which is derived from an *Escherichia* cell or an *S. cerevisiae* cell.

* * * * *